United States Patent [19]

Elliott

[11] Patent Number: 4,479,075
[45] Date of Patent: Oct. 23, 1984

[54] CAPACITATIVELY COUPLED PLASMA DEVICE

[76] Inventor: William G. Elliott, 60 Baker Bridge Rd., Lincoln, Mass. 01773

[21] Appl. No.: 327,031

[22] Filed: Dec. 3, 1981

[51] Int. Cl.$^3$ .................. H01J 7/24; H05B 31/26
[52] U.S. Cl. .................. 315/111.21; 219/121 PM; 313/607; 315/111.11
[58] Field of Search .............. 219/121 PM; 313/201, 313/202, 203, 231.31, 231.41, 231.51; 315/111.1, 111.2, 111.4; 356/316

[56] References Cited

U.S. PATENT DOCUMENTS 3,596,128 7/1971 Elliott .
4,009,413 2/1977 Elliott et al. ............. 315/111.21
4,147,957 4/1979 Hildebrand .

OTHER PUBLICATIONS

K. A. Egorova; Use of a High Frequency Electrodeless Discharge in the Analysis of Solutions; Zhurnal Prikladnoi Spectroskopii, vol. 6, No. 1, pp. 22–26; 1967.
A. V. Zvyagintsev et al.; Electrodeless Capacitative Arc; Sov. Phys. Tech. Phys.; vol. 20, No. 2.
N. I. Gondar et al.; Electrodeless Plasma Generator with Capacitative Arc Discharge; Sov. Phys. Tech. Phys.; vol. 20, No. 3; pp. 407–408.

*Primary Examiner*—Eugene R. LaRoche
*Assistant Examiner*—Robert E. Wise
*Attorney, Agent, or Firm*—Frank A. Steinhilper

[57] ABSTRACT

A capacitatively coupled plasma device has a plasma tube, an electrode positioned near the tube and means to supply a high voltage, high frequency potential such as a radio frequency to the tube to energize a flow of argon or like gas to form a plasma. A sample of material is excited by the plasma energy to emit characteristic radiation for analysis by suitable means such as spectrometric analysis or for other use and application.

13 Claims, 4 Drawing Figures

U.S. Patent    Oct. 23, 1984    4,479,075

CAPACITATIVELY COUPLED PLASMA DEVICE

BACKGROUND OF THE INVENTION

Various methods are known for the formation of a plasma or ionized gas. Frequently a plasma is employed for chemical reaction or in connection with chemical analysis, and for such purposes the most often used methods of plasma generation are direct conduction of electric charge into an ionizable gas or inductive coupling by means of an appropriate magnetic field. Also sometimes employed is microwave energization by means of an appropriate wave energy in a resonant cavity. In all of these, a gas discharge is energized, causing ionization of the gas, the most frequently employed gas for this purpose being argon or other so-called inert gas.

One valuable use and application of plasma generators in recent years has been for spectrographic or spectrometric analysis of trace material in a sample, and the present invention while not limited to this purpose is aimed at such use. For this application of plasma, a small sample of a material to be tested is brought into the near vicinity, or within the field of energy, of a plasma jet, causing the sample to become energized to emit identifiably characteristic radiation. By means of a spectrometer or other radiation-identifying means this radiation is identified and measured, thus identifying and quantifying the nature of the element or other material in the sample. For this purpose it is important to have a small sized plasma jet so that as small a sample as possible can be analyzed and to have the reaction or analyzing area small, compact, and uniformly reproducible. It is also important to keep the plasma device free from contamination, particularly to keep it free from contaminants which may remain in the equipment for protracted periods of time.

One plasma jet device which has found commercial use for such spectrometric analysis is that of Elliott et al U.S. Pat. No. 4,009,413. According to that patent, a plasma is formed in the shape of an inverted V by means of anode and cathode electrodes which direct jets of argon or similar gas to form a plasma having a bend or elbow. A sample to be analyzed is fed into the pocket of the elbow where it is energized by the plasma and is thus caused to emit its characteristic radiation.

One difficulty with this type of device, believed to be inherent in its anode-cathode nature, is that the electrodes erode, thus requiring frequent replacement and/or adjustment and, in addition, running the risk of introducing contamination in the form of the anode or cathode material.

GENERAL NATURE OF THE INVENTION

According to the present invention, a plasma is generated in a small plasma jet device wherein an ionizable gas such as argon, helium or the like is fed through a tube or other jet-forming member and is capacitatively coupled to a high frequency field such as a radio frequency field. Gasses of other types can be employed, including air, or if cost is not a major factor, other so-called inert gases such as neon.

In one embodiment of the invention, presently preferred, two or more jet forming members are employed, the two members being aimed to meet at a common point or joint, forming a bent plasma. In this embodiment, a sample to be analyzed in spectrometric or other analysis can be separately directed into the pocket of this bent plasma, or the sample to be analyzed or treated may be introduced into the effective field of the energy of the plasma by introduction before, during, or after its ionization. In one form of the invention in which a bent plasma is formed, the sample may be fed to the pocket of the bend in the plasma.

The plasma jet device according to the present invention has numerous advantages, one of which in contrast to the anode-cathode type of generator, is that the present device and the capacitative way of energizing the device does not cause electrode erosion with its consequent need for adjustment and its consequent introduction of contaminants into the plasma.

The sample being analyzed or treated may be a solid positioned within or near the plasma path, it may be a liquid or powder such as an aerosol or a powder dispersed in a gas, or it may be another form of sample within or near the plasma. In particular, when the sample is a gas, liquid or powder, it may be sprayed into the elbow of a bent plasma or it may be incorporated within the plasma gas in the plasma jet device, but it is not substantially intermixed with and blended into the plasma. Accordingly, the invention includes the method of combining the plasma gas and the sample. Thus a dispersion or a solution of the sample material may be atomized or nebulized and either passed close to the plasma or directed within or around the plasma path, or it may be introduced directly within the plasma gas, for example concentrically within the plasma gas in the plasma tube. In one form of the invention, a nebulized liquid sample is mixed with carrier gas such as argon and the mixture is passed through the center of the plasma device. Plasma devices intermixing sample and plasma gas are not inoperative, but the presently preferred embodiment of the invention minimizes such intermixing.

The general nature of the invention having been set forth, the invention is more fully described in connection with the drawings in which.

SPECIFIC DESCRIPTION OF THE INVENTION

Figure 1:
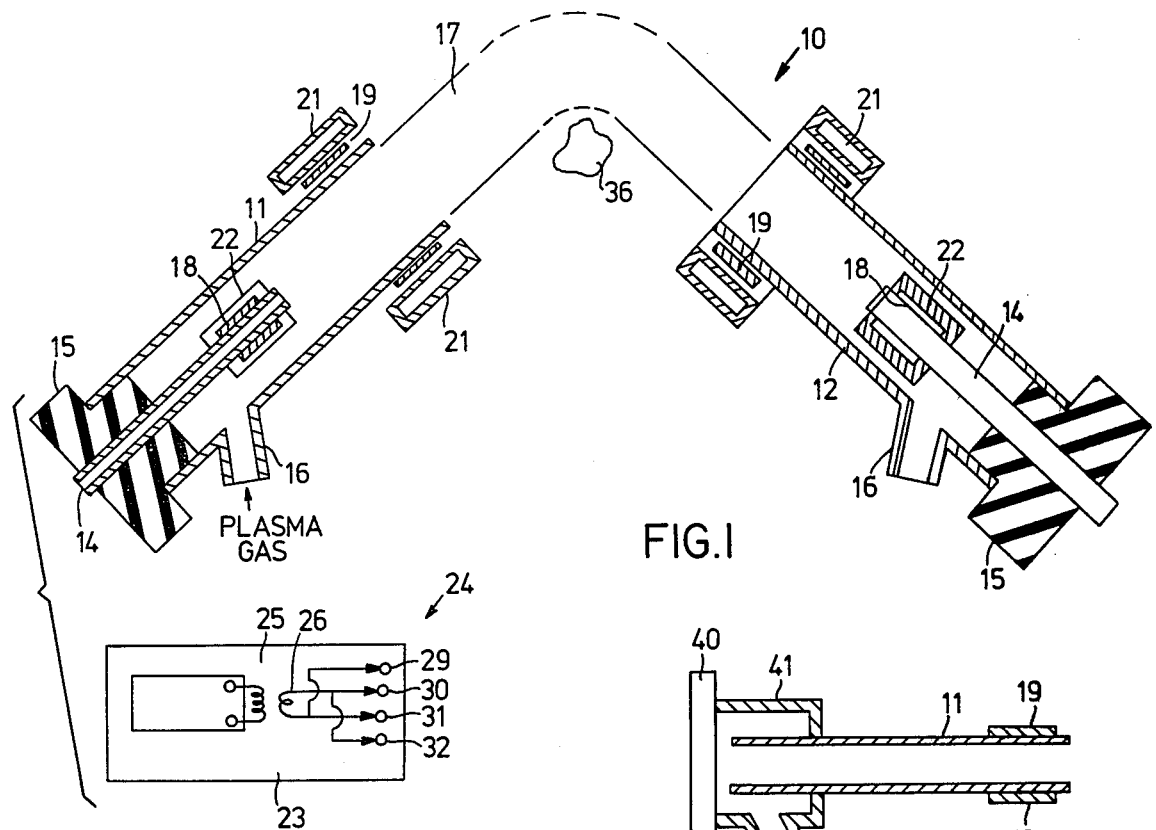
FIG. 1 is a diagrammatic view of a plasma jet device according to one embodiment of the invention.

In FIG. 1 is illustrated a plasma jet device generally designated 10, having two plasma jet tubes 11 and 12 of a suitable material such as, for example, quartz tubes or the like. These tubes are mounted on adjustable mounts (not shown) to permit the tubes to be aimed in a desired direction and adjusted in position for optimum location and direction. As shown, the two tubes 11 and 12 are aimed at an angle with respect to one another to direct a flow from the tubes to meet at a point representing the vertex of a V. Each tube has a post 14 projecting into the tube 11 or 12 through a mounting block 15 such as a Teflon block. The mounting block is snugly fitted around the post 14 and snugly fitted into the tube 11 or 12.

Each tube has side arm 16 or other suitable means positioned to direct a flow of ionizable gas around post 14 and out the end of the tube. In this manner, there is a flow of gas in a bent or V-shaped configuration which in operation yields a bent plasma 17. Mounted on post 14 is an electrode 18, one such electrode 18 being in each of tubes 11 and 12. Positioned around each tube 11 and 12 is a cylindrical electrode 19, near the open or front end of the tube. The distance between electrode 18 and electrode 19 is set for optimum performance, and distances of 5 millimeters or less, or even with electrode 18 positioned within electrode 19 have been found operable, as have substantially greater distances. Electrode 18 may, if desired, be contained in an insulating jacket or tube 22 surrounding the electrode.

Cooling means (not shown) is provided to keep tubes 11 and 12 and the electrodes from overheating. Simple cooling means may be a flow of water through water jackets 21 around each electrode 19. If desired, electrode 18 may also be cooled.

A high frequency, high potential power source generally designated 23 has a radio frequency power source generally designated 24 with a primary coil 25 and a secondary coil 26 connected to four output terminals 29, 30. 31, and 32; posts 29 and 31 being connected to the opposite output of coil 26. Post or terminal 29 is connected in turn to inner electrode 18 of tube 11 and its corresponding terminal 31 is connected to the outer electrode of the other tube 12; similarly, terminal 30 is connected to the inner electrode 18 of tube 12 and terminal 32 to the outer electrode of tube 11. Thus, in each tube the electrical connections to the inner electrode 18 and the outer electrode 19 are of opposite phase, while the two outer electrodes are themselves oppositely connected. Other methods of providing radio frequency energy to the plasma electrodes may employ direct connections to the primary coil or other forms of apparatus for impedance matching.

Figure 2:
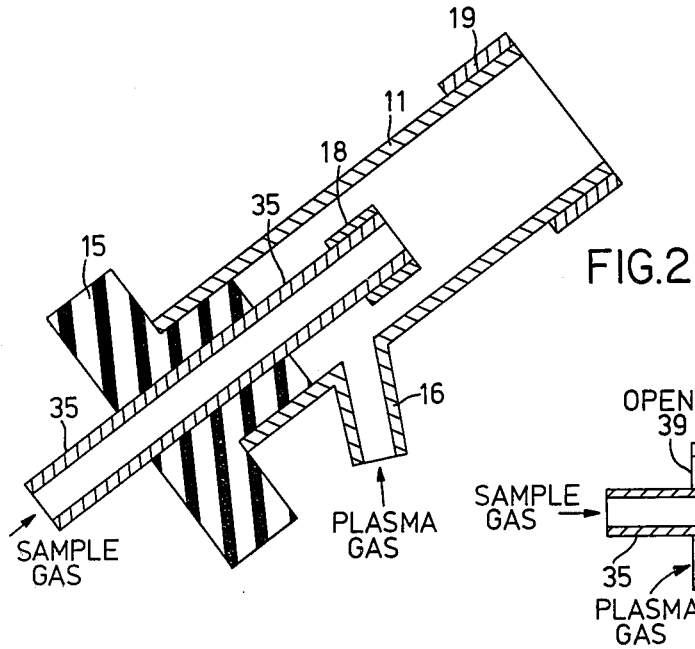
FIG. 2 is a diagrammatic view of a plasma jet tube according to another embodiment of the invention.

In FIG. 2 is illustrated an embodiment of the invention in which tube 11 (similar to tube 11 of FIG. 1) has an outer cylindrical electrode 19 near the front thereof and a side arm 16 near its rear end, all as in FIG. 1. In this case, however, a tube 35 is positioned within mounting block 15, projecting from outside tube 11 through block 15 and into the tube 11 concentrically therewith. Mounted around the end of tube 35 is an inner cylindrical electrode 18. If desired, the second electrode 18 may be positioned along the outer tube 11 and spaced longitudinally from electrode 19. As illustrated, tube 35 is hollow and a gas containing a sample to be analyzed or treated is fed through tube 35 and concentrically along inside tube 11. An ionizable gas such as argon is fed around tube 35, forming a hollow cylinder of plasma gas surrounding tube 35 and surrounding the inner sample gas. Thus the resulting plasma jet 17 (see FIG. 1) has the sample within itself with minimal intermixing or blending of plasma and sample. Apparatus may comprise two such tubes 11, mounted in the configuration shown in FIG. 1 to form a bent plasma.

Referring now to FIG. 1, a sample 36 to be analyzed or treated is positioned close to the plasma jet 17. In the case of a solid sample, the sample itself may be mounted near the plasma jet 17, or in the case of a gaseous sample, a flow of the sample-containing gas is directed alongside the plasma jet, preferably at the elbow of the bent plasma shown in FIG. 1. In such case, the sample gas which is directed toward the plasma may envelop such jet, and in the structure illustrated in FIG. 2 the sample will be concentrically alongside but inside the plasma jet.

Figure 3:
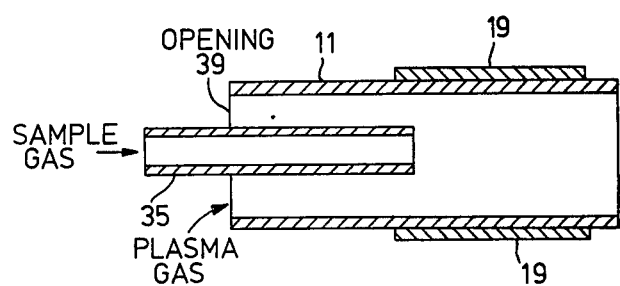
FIG. 3 is a diagrammatic view of a plasma jet tube according to still another embodiment of the invention.

In FIG. 3 is shown another embodiment of the invention in which a plasma jet tube 11 has an outer cylindrical electrode 19 positioned therearound and a hollow sample tube 35 projecting into one end thereof. An opening 39 around tube 35 provides feed of argon or other plasma gas in a hollow cylindrical form adjacent the wall of tube 11 while sample gas is fed concentrically through the center of tube 11 in the absence of substantial mixing between the plasma gas and sample gas. The sample gas may have argon as its suspending gas without providing substantial mixing with the plasma. While tube 11 of this FIG. 3 has an outer cylindrical electrode 19, there is no inner electrode corresponding to electrode 18 of FIG. 1. A high frequency power supply such as power supply 23 of FIG. 1 is connected to electrode 19; the opposite pole of a power supply may be connected to earth or elsewhere in the apparatus.

Figure 4:
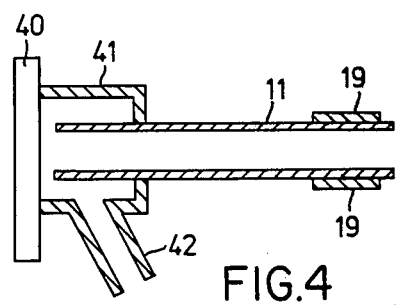
FIG. 4 is a diagrammatic view of a plasma jet tube according to another embodiment of the invention with a solid sample material.

In FIG. 4, a plasma tube 11 has an outer cylindrical electrode 19. At one end of tube 11 an enclosure 41 surrounds tube 11 and a gas channel 42 directs a flow of plasma gas through enclosure 41. A solid element 40, which may be a sample to be analyzed or treated is positioned against enclosure 41 and is located and adapted to have plasma jet flow along the surface of element 40. Element 40 and electrode 19 are connected to a high frequency power supply such as power supply 23 of FIG. 1, causing element 40 to act as one of two electrodes in the plasma jet device. In this embodiment of the invention, sample element 40 is energized by the plasma jet and can be spectrometrically analyzed.

Referring now to FIG. 1, it is observed that electrode 18 in this configuration provides a strong electric field to ignite the primary discharge between the pair of electrodes 19. Consequently current limiting components may be introduced into the electrical components or electrical circuitry such as between the high frequency, high voltage generator 23 and electrode 18. In some structures and devices, such as that illustrated in FIG. 3, one or both electrodes 18 may be omitted, and in such instances other means such as a spark may be employed for igniting the primary discharge.

The plasma device according to this invention is small and compact. It is generally well adapted to operation in conjunction with spectroscopic and spectrometric analysis for detection and measurement of trace quantities of materials or impurities in a sample of extremely small size. It is also adapted for energizing a sample material for other uses and applications. In contradistinction from many other plasma devices, the present device produces a plasma jet which is less than about $\frac{1}{4}$ inch in diameter and may be about one or two inches long. The power consumption is generally in the order of a fraction of one kilowatt, generally in the range of about 200 watts. The rf frequency is easily shielded and thus does not represent significant disturbance to communications systems utilizing transmitted radio frequencies.

These size and power characteristics of the device are of important practical advantage, inasmuch as they permit the use of the equipment in laboratory environments and in commercial and industrial environments where size itself may be disadvantageous and where power dissipation and radio frequency leakage would interfere with the use of the plasma device for its intended purpose.

I claim:

1. A capacitatively coupled plasma jet device comprising at least one tube of electrically insulating material,
   a cylindrical electrode outside and substantially surrounding said tube,
   means to flow an ionizable gas tangentially through said tube,
   a solid electrically conducting sample positioned adjacent to the gas flow of said tube,
   and means to apply a high voltage, high frequency electric potential between said electrode and said sample.

2. In a capacitatively coupled plasma jet device, a plasma jet tube of insulating material, means to feed an ionizable gas tangentially through said tube, a first cylindrical electrode outside and surrounding said tube, a second coaxial cylindrical electrode within said tube and mounted and positioned such that the flow of ionizable gas is between said first and second coaxial cylindrical electrodes, and means to apply a high voltage, high frequency electric potential to said first and second electrodes, whereby the flow of ionizable gas is in a high potential high frequency field and is thereby ionized to form a hollow cylindrical plasma flow.

3. The capacitatively coupled plasma jet device of claim 2, wherein said high voltage, high frequency field is radio frequency.

4. The capacitatively coupled plasma jet device of claim 2, wherein said second electrode is enclosed in an insulating jacket.

5. A capacitatively coupled plasma jet device according to claim 2 having means to introduce a sample into the central region of the hollow cylindrical plasma.

6. A capacitatively coupled plasma device comprising
   a first tube of electrically insulating material,
   at least one cylindrical electrode outside and surrounding said tube,
   a second inner tube mounted and positioned within said first tube,
   means to flow an ionizable gas tangentially through said first tube, within said first tube and around said second tube,
   means to flow a sample-containing gas through said second tube and within the flow of said ionizable gas, and
   means to supply a high voltage, high frequency electric potential to said electrode.

7. The capacitatively coupled plasma device of claim 6, having a single electrode and means to supply to said electrode a high voltage, high frequency potential to said electrode relative to earth.

8. The capacitatively coupled plasma device of claim 6 in which an ionizable plasma gas and a sample material are directed to flow through said tube and maintained essentially independently without mixing together.

9. A capacitatively coupled plasma jet device comprising
   a first tube of electrically insulating material,
   a first electrode positioned adjacent to said tube and at least partially surrounding said first tube,
   a second tube of electrically insulating material,
   a second electrode positioned adjacent to said second tube and at least partially surrounding said second tube,
   said first tube and said second tube being directed and positioned to direct flows of gas to join each other to form a continuous column of said gas,
   means to apply a high voltage, high frequency potential to the first and second electrodes,
   means to feed an ionizable gas through said first tube and to feed an ionizable gas through said second tube to form a continuous column of ionizable gas, and
   means to introduce a sample into the area of influence of said jet of ionizable gas,
   whereby said ionizable gas is ionized to form a plasma column and said sample is energized.

10. The capacitatively coupled plasma jet device of claim 9, wherein said high voltage, high frequency potential is radio frequency.

11. The capacitatively coupled plasma jet device of claim 9, wherein the sample is in the form of a flow of a gas containing a sample, and said sample-containing gas is directed adjacent to said plasma jet.

12. A capacitatively coupled plasma jet device of claim 9 having means to generate a gas suspension of finely divided sample and means to direct said suspension into the area of energy of said plasma column within at least one of said tubes.

13. The capacitatively coupled plasma device of claim 9, having an inner electrode positioned within at least one of said tubes and means to apply a high voltage, high potential between said inner electrode and an outer electrode outside said same tube.

* * * * *